US00PP17856P2

(12) United States Plant Patent
Dekker

(10) Patent No.: US PP17,856 P2
(45) Date of Patent: Jul. 10, 2007

(54) ***CHRYSANTHEMUM* PLANT NAMED 'DEKPROUD'**

(50) Latin Name: *Chrysanthemum×morifolium*
Varietal Denomination: Dekproud

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 93 days.

(21) Appl. No.: 11/178,268

(22) Filed: Jul. 8, 2005

(51) Int. Cl.
*A01H 5/00* (2006.01)

(52) U.S. Cl. ..... Plt./297

(58) Field of Classification Search ..... Plt./297
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Dekproud', characterized by its anemone-type inflorescences with lanceolate-shaped, pink-colored ray florets; green to pink-colored disc florets with yellow-colored apices; strong and upright flowering stems; freely flowering habit; early and uniform flowering response; and good postproduction longevity.

2 Drawing Sheets

Botanical designation: *Chrysanthemum×morifolium.*
Cultivar denomination: 'Dekproud'.

BACKGROUND OF THE INVENTION

The present invention relates to a new and distinct cultivar of *Chrysanthemum* plant, botanically known as *Chrysanthemum×morifolium* and referred to by the name 'Dekproud'.

The new *Chrysanthemum* is the product of a planned breeding program conducted by the Inventor in Hensbroek, The Netherlands. The objective of the breeding program is to create new cut *Chrysanthemum* cultivars with interesting inflorescence forms and attractive floret coloration.

The new *Chrysanthemum* originated from a cross-pollination made by the Inventor on Mar. 27, 2002, in Hensbroek, The Netherlands, of a proprietary selection of *Chrysanthemum* identified as code number 5003.49, not patented, as the female, or seed, parent with a proprietary *Chrysanthemum* selection identified as code number 99.795.01, not patented, as the male, or pollen, parent. The new *Chrysanthemum* was discovered and selected by the Inventor as a single plant within the progeny of the stated cross-pollination in a controlled environment in Hensbroek, The Netherlands.

Asexual reproduction of the new *Chrysanthemum* by terminal cuttings in Hensbroek, The Netherlands since November, 2002, has shown that the unique features of this new *Chrysanthemum* are stable and reproduced true to type in successive generations.

BRIEF SUMMARY OF THE INVENTION

The cultivar Dekproud has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekproud'. These characteristics in combination distinguish 'Dekproud' as a new and distinct cultivar:

1. Anemone-type inflorescences with lanceolate-shaped, pink-colored ray florets; green to pink-colored disc florets with yellow-colored apices.
2. Strong and upright flowering stems.
3. Freely flowering habit.
4. Early and uniform flowering response.
5. Good postproduction longevity.

Plants of the new *Chrysanthemum* can be compared to plants of the female parent selection. In side-by-side comparisons conducted in Hensbroek, The Netherlands, plants of the new *Chrysanthemum* differed from plants of the female parent selection in the following characteristics:

1. Plants of the new *Chrysanthemum* were more vigorous than plants of the female parent selection.
2. Plants of the new *Chrysanthemum* had larger leaves than plants of the female parent selection.
3. Ray florets of plants of the new *Chrysanthemum* were lighter pink in color than ray florets of plants of the female parent selection.

Plants of the new *Chrysanthemum* can be compared to plants of the male parent selection. In side-by-side comparisons conducted in Hensbroek, The Netherlands, plants of the new *Chrysanthemum* differed from plants of the male parent selection in the following characteristics:

1. Plants of the new *Chrysanthemum* were more vigorous than plants of the male parent selection.
2. Plants of the new *Chrysanthemum* had smaller leaves than plants of the male parent selection.
3. Plants of the new *Chrysanthemum* had larger inflorescences than plants of the male parent selection.
4. Plants of new *Chrysanthemum* and the male parent selection differed in ray floret coloration as plants of the male parent selection had white-colored ray florets.

Plants of the new *Chrysanthemum* can be compared to plants of the *Chrysanthemum* cultivar Mona Lisa Rosy, not patented. In side-by-side comparisons conducted in Hensbroek, The Netherlands, plants of the new *Chrysanthemum* differed primarily from plants of the cultivar Mona Lisa Rosy in the following characteristics:

1. Leaves of plants of the new *Chrysanthemum* were rougher than leaves of plants of the cultivar Mona Lisa Rosy.
2. Plants of the new *Chrysanthemum* had fewer inflorescences per flowering stem than plants of the cultivar Mona Lisa Rosy.
3. Ray florets of plants of the new *Chrysanthemum* were darker pink in color than ray florets of plants of the cultivar Mona Lisa Rosy.
4. Plants of the new *Chrysanthemum* had longer disc florets than plants of the cultivar Mona Lisa Rosy.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum*.

The photograph on the first sheet comprises a side perspective view of a typical flowering stem of 'Dekproud'.

The photograph at the top of the second sheet is a close-up view of typical inflorescences of 'Dekproud'.

The photograph at the bottom of the sheet is a close-up view of upper and lower surfaces of typical inflorescences and typical leaves of 'Dekproud'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter and early spring in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5 to 30° C., night temperatures ranged from 18.5 to 24° C. and light levels were about five kilolux. Plants were pinched once and were about ten weeks from planting when the photographs and the description were taken.

Botanical classification: *Chrysanthemum×morifolium* cultivar Dekproud.

Commercial classification: Anemone-type *Chrysanthemum* typically grown as a spray-type cut flower.

Parentage:

*Female or seed parent.*—Proprietary selection of *Chrysanthemum×morifolium* identified as code number 5003.49, not patented.

*Male or pollen parent.*—Proprietary selection of *Chrysanthemum×morifolium* identified as code number 99.795.01, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine; light brown in color.

*Rooting habit.*—Freely branching.

Plant description:

*Appearance.*—Herbaceous anemone-type cut *Chrysanthemum;* typically grown as a spray-type; erect and strong flowering stems. Vigorous.

*Flowering stem description.*—Length: About 80 cm. Diameter: About 6 mm. Strength: Strong. Texture: Pubescent. Aspect: Erect. Branching habit: Plants are typically grown as single stems. Color: 146A.

*Foliage description.*—Arrangement: Alternate. Length: About 6.5 to 9.5 cm. Width: About 5 to 6.5 cm. Apex: Mucronate. Base: Mostly truncate. Margin: Pinnately lobed. Texture, upper and lower surface: Pubescent; rough. Petiole length: About 2.5 to 3 cm. Color: Developing foliage, upper surface: Darker than 147A. Developing foliage, lower surface: Close to 137B. Fully expanded foliage, upper surface: Darker than 147A. Fully expanded foliage, lower surface: Close to 147B. Venation, upper surface: 147B. Venation, lower surface: 146A. Petiole, upper and lower surfaces: 146A.

Inflorescence description:

*Appearance.*—Anemone-type inflorescence form with lanceolate-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 7.5 weeks later. Early and uniform flowering response.

*Postproduction longevity.*—Cut inflorescences will maintain good substance and form for about 3.5 weeks.

*Quantity of inflorescences per flowering stem.*—About 15 to 20 inflorescence per flowering stem.

*Inflorescence size.*—Diameter: About 6.5 cm. Depth (height): About 2.5 to 3 cm. Diameter of disc: About 2.2 cm.

*Inflorescence buds.*—Height: About 7 mm. Diameter: About 1 cm. Shape: Oblate. Color: Close to 138A.

*Ray florets.*—Length: About 2.5 to 3 cm. Width: About 1 cm. Shape: Lanceolate. Apex: Acute to rounded. Base: Acute; fused. Margin: Entire. Texture, upper and lower surfaces: Smooth, glabrous; undulate. Number of ray florets per inflorescence: About 26. Color: When opening, upper surface: 77D. When opening, lower surface: 69B. Fully opened, upper surface: 84B to 84C. Fully opened, lower surface: 84C to 84D.

*Disc florets.*—Shape: Tubular; enlarged. Length: About 7 mm to 22 mm. Width: About 1 mm to 3 mm. Number of disc florets per inflorescence: About 140. Color: Immature: 145C. Mature: Apex: 6A. Midsection: 84B. Base: N144D.

*Peduncles.*—Length, terminal peduncle: About 4.5 cm. Length, fourth peduncle: About 7.5 cm. Diameter:

About 2 to 4 mm. Angle: About 45° from vertical. Strength: Moderately strong. Texture: Pubescent. Color: 147B.

*Reproductive organs.*—Androecium: Present on disc florets only. Anther color: Close to 9A. Pollen color: Close to 9A. Gynoecium: Present on both ray and disc florets. Stigma length: About 1 mm. Stigma diameter: About 0.3 mm. Stigma color: Close to 144C to 144D.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Dekproud', as illustrated and described.

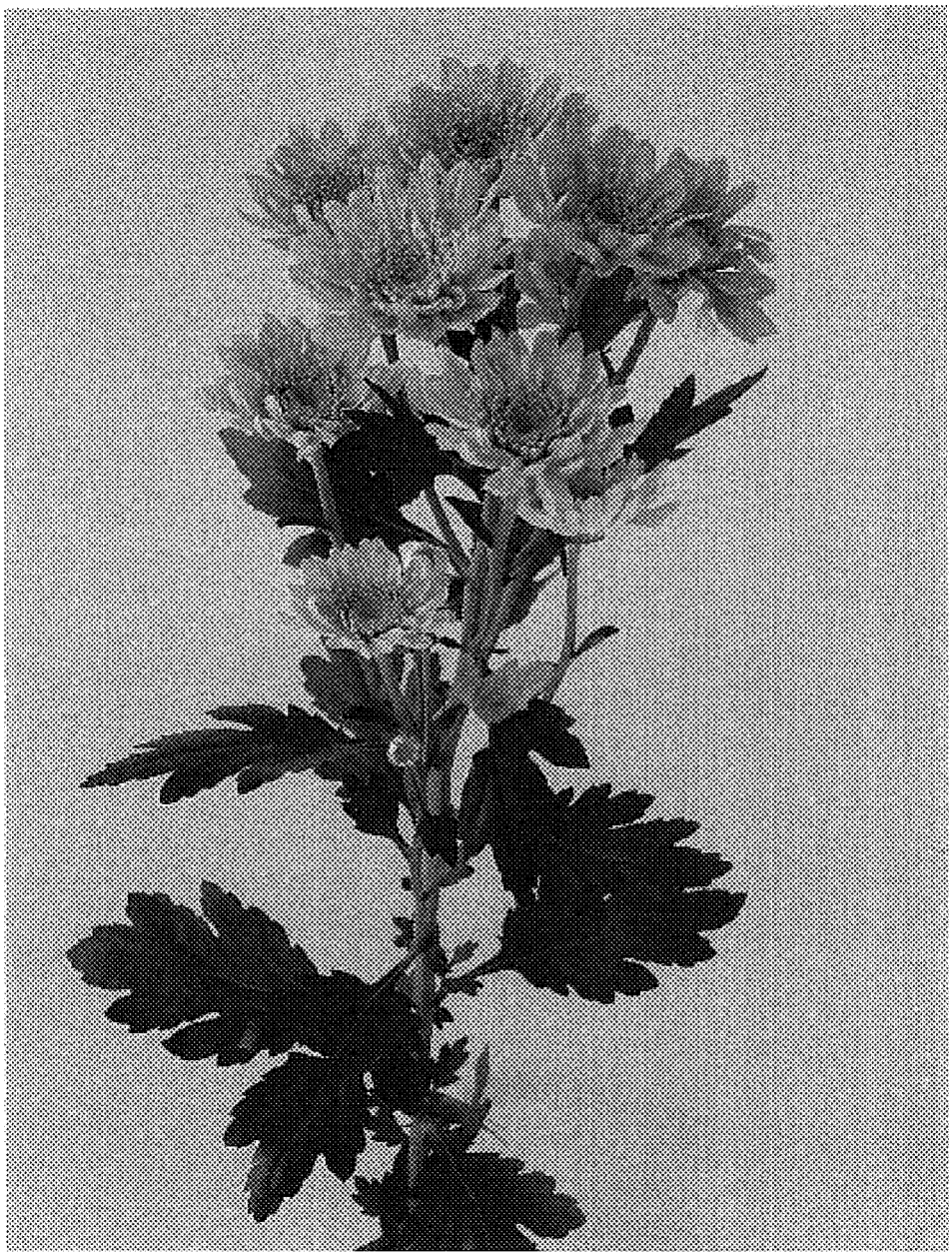

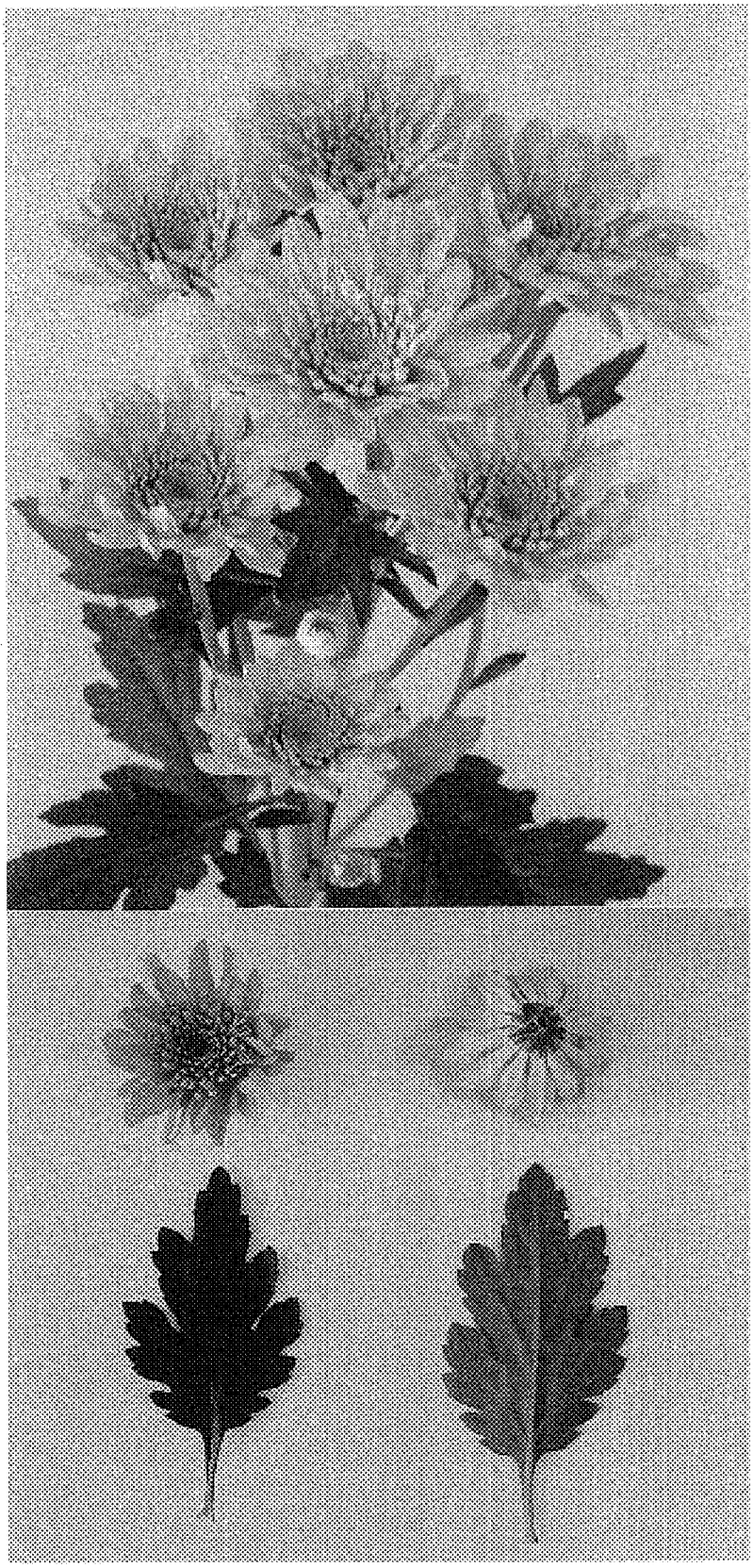

* * * * *